United States Patent [19]
Montagnier et al.

[11] Patent Number: 4,798,797
[45] Date of Patent: Jan. 17, 1989

[54] RETROVIRUS ASSOCIATED WITH LYMPHADENOPATHIES AND ADAPTED TO CONTINUOUS LINES OF LYMPHOBLASTOID B CELLS, CAPABLE OF PRODUCING RETROVIRUS CONTINUOUSLY AND PROCESS FOR THEIR PRODUCTION

[75] Inventors: Luc Montagnier, Le Plessis Robinson; Solange Chamaret, Paris; Jacqueline Gruest, L'Hay Les Roses, all of France

[73] Assignee: Institut Pasteur, Paris, France

[21] Appl. No.: 922,764

[22] Filed: Oct. 24, 1986

Related U.S. Application Data

[63] Continuation of Ser. No. 731,847, May 8, 1985, abandoned, which is a continuation-in-part of Ser. No. 558,109, Dec. 5, 1983, abandoned, and a continuation-in-part of Ser. No. 706,562, Feb. 28, 1985, abandoned, and a continuation-in-part of Ser. No. 712,959, Mar. 18, 1985, abandoned.

[30] Foreign Application Priority Data

May 9, 1984 [FR] France ................ 84 07151

[51] Int. Cl.$^4$ .................. C12N 7/00; C12N 5/00; A61K 39/00; C12Q 1/70
[52] U.S. Cl. ................... 435/235; 435/236; 435/237; 435/240.1; 435/240.2; 435/5; 435/948; 424/89
[58] Field of Search ............ 435/240, 241, 235–239, 435/810, 4, 5, 7, 29, 68, 70, 188, 948, 240, 241, 240.2; 424/85, 86, 88, 89, 93; 436/810, 809, 510, 518, 536, 542, 543, 547, 800, 804, 808, 811, 815, 823, 828; 530/403; 422/61

[56] References Cited

U.S. PATENT DOCUMENTS

| 4,520,113 | 5/1985 | Gallo et al. | 436/504 |
|---|---|---|---|
| 4,647,773 | 3/1987 | Gallo et al. | 435/239 |
| 4,652,599 | 3/1987 | Gallo et al. | 435/239 |
| 4,708,818 | 11/1987 | Montagnier et al. | 435/5 |
| 4,716,102 | 12/1987 | Levy | 435/5 |

OTHER PUBLICATIONS

Montagnier, L. et al., Science 225:63–66 (Jul. 6, 1984).
Brun-Vezinet, F. et al., Science 226:453–456 (Oct. 26, 1984).
Barré-Siroussi, F. et al., Science 220:868–871 (May 20, 1983).
Montagnier, L. et al., *Human T Cell Leukemia Lymphoma Viruses*, CSH, NY, Gallo, P. C. et al., eds. (1984), pp. 363–379.
Science, vol. 225, Jul. 6, 1984, pp. 63–66.
Proc. NATL. ACAD. SCI., vol. 81, Jan. 1984, pp. 33–37, Biochemistry, US; R. D. Lasky et al., "Possible DNA–RNA Tumor Virus Interaction in Human Lymphomas: Expression of Retroviral proteins in Ramos Lymphoma Lines is Enhanced After Conversion with Epstein–Barr Virus".
NATURE, vol. 309, May 3, 1984, pp. 12–13, Chesham, Bucks, GB, R. Weiss, "Acquired Immune Deficiency Syndrome: Retroviruses linked with AIDS".
SCIENCE, vol. 224, No. 4648, May 4, 1984, pp. 497–500, M. Popovic et al., "Detection, Isolation, and Continuous Production of Cytopathic Retroviruses (HTLV-III) from patients with AIDS and pre-AIDS".
SCIENCE, vol. 220, No. 4599, May 20, 1983, pp. 868–871, F. Barre-Sinoussi et al., "Isolation of a T–Lymphtropic Retrovirus from a Patient at risk for Acquired Immune Deficiency Syndrome (AIDS)".
SCIENCE, vol. 225, No. 4657, Jul. 6, 1984, pp. 63–66, L. Montagnier et al., "Adaption of Lymphadenopathy Associated Virus (LAV) to Replication in EBV-Transformed B Lymphoblastoid Cell Lines.

*Primary Examiner*—Margaret Moskowitz
*Attorney, Agent, or Firm*—Finnegan, Henderson, Farabow, Garrett & Dunner

[57] ABSTRACT

A retrovirus B-LAV associated with lymphadenopathies and with Acquire Immune Deficiency Syndrome, being adapted to B lymphocytes and capable of being continuously produced by continuous cell lines of B lymphoblastoid cells; continuous cell lines of B lymphoblastoid cells which produce the B-LAV retrovirus and a process for producing such cell lines are disclosed.

31 Claims, No Drawings

RETROVIRUS ASSOCIATED WITH LYMPHADENOPATHIES AND ADAPTED TO CONTINUOUS LINES OF LYMPHOBLASTOID B CELLS, CAPABLE OF PRODUCING RETROVIRUS CONTINUOUSLY AND PROCESS FOR THEIR PRODUCTION

CROSS-REFERENCE TO RELATED APPLICATIONS

This application is a continuation of application Ser. No. 731,847, filed May 8, 1985, now abandoned, which in turn is a continuation-in-part of application Ser. No. 558,109, filed Dec. 5, 1983, which is now abandoned, and Ser. No. 706,562, filed Feb. 9, 1985, which is now abandoned, and Ser. No. 712,959, filed Mar. 18, 1985, which is also abandoned.

The invention relates to a retrovirus associated with lymphadenopathies, called below retrovirus LAV (abbreviation of the English expression "Lymphadenopathy Associated Virus") this retrovirus being adapted to B lymphocytes and capable of being produced continuously by continuous lines of B lymphoblastoid cells growing in suspension. It relates more particularly to continuous lines of B lymphoblastoid cells which can replicate a retrovirus having the antigen characteristics of the LAV virus and to a process for producing such cell lines.

The invention relates naturally also to extracts which can be obtained from such viruses, more particularly those which can be recognised by the serums of patients suffering form the acquired immunodeficiency syndrome (AIDS) or by syndromes bringing lymphadenopathies into action, or other precursor signs of AIDS, denoted below by the abbreviation SLA. For this reason it relates to any possible uses of this virus and these extracts, particularly those intended for the detection of the presence of this virus in biological specimens, and more particularly for the in vitro diagnosis of SLAs and of AIDS.

AIDS is an infection which has recently developed in several countries. It has been observed that AIDS was often accompanied or preceded by recognisable lymphadenopathic syndromes, on the occasion of histological study of the lymph nodules in patients afflicted by it. These lymphadenopathies precede or perhaps constitute a less serious form of the disease, which, in its final stage, is manifested by a collapse of the immune defenses of the subject accompanied by the appearance of a Kaposi sarcoma or opportunist infections.

The isolation of a retrovirus considered as the major etiological agent of AIDS and of SLAs has been described by S. BARRE-SINOUSSI et Coll. in an article entitled "Isolation of a T-lymphotropic retrovirus from a patient at risk for acquired immune deficiency syndrome (AIDS)", Science 220, 868–70 (1983). This retrovirus has been isolated from a T lymphocyte culture obtained from a lymph nodule of a homosexual having an SLA. The virus isolates have since been isolated from lymph nodules obtained from other persons suffering from AIDS, among which are a B hemophiliac.

The principal characteristics of this retrovirus will be recalled below:

The preferred targets of this retrovirus are constituted by T lymphocytes, more particularly Leu-3 cells, It is manifested by a reverse transcriptase action depending on the presence of $Mg^{2+}$ ions, this reverse transcriptase possessing a strong affinity for poly-(adenglate-oligodeoxy thymidylate) [poly(A)oligo(dT)-12-18], It has an average diameter of 139 nanometers and it possesses an eccentric nucleus having an average diameter of 41 nanometers, It induces the production in the cell that it infects of a p25 viral protein, having a molecular weight of the order of 25,000, this p25 protein not being recognised by antibodies previously formed against p24 protein, isolated under similar conditions from cells infected by a virus of the HTLV type [human T cell Leukemia virus described in "Journal of National Cancer Institute", 1982, vol. 69 No. 6 by Gallo and Reitz and in "Cold Spring Harbour Laboratories", 1984, Human T cell Leukemia Lymphoma virus, by Gallo, Essex and Gross] more particularly HTLV1 and HTLV2, It shows weak antigen homology with the virus of infectious anaemia virus of the horse (VAIC), in that the antibodies formed against the latter virus immunoprecipitate the abovesaid p25 protein from the LAV virus, and It has a density of the order of 1.16 in a sucrose gradient.

It has also been shown in the article mentioned above that the virus could be propagated in T lymphocyte cultures derived preferably from a healthy adult donor or from an umbilical cord. The conditions in which the lymphocytes can be infected have been described in the above-mentioned article. Advantageously this infection is caused in the presence of a human anti-α-interferon serum. The virus production evaluated by means of its reverse transcriptase action, generally starts between the 9th and 15th day following the date of infection and continues for a period of 10 to 15 days.

Specimens representative of the two LAV retroviruses were deposited at the CNCM on Sept. 15, 1983 under numbers 1-240 and 1-241 respectively.

This being the case one of the difficulties which it has not been possible to overcome hitherto resides in the difficulty of replicating the LAV retrovirus in large amounts in T lymphocytes. In fact no permanent line of cells continuously productive of the LAV virus has been isolated. The production of LAV virus is only transitory and the latter finish by killing the host cell, so that the production of further doses of virus is each time tributary on fresh T lymphocytes cultures. Lastly, the efficient in vitro replication of the virus involves the presence in the culture medium of an expensive growth factor, known under the name TCGF (abrreviation of the expression "T cell growth factor") or also called interleukine II.

SUMMARY OF THE INVENTION

It is an object of the invention to overcome these difficulties, in particular to provide cell lines both permanent directly infectable by a retrovirus possessing the essential immunological characteristics of the LAV virus and possessing also the capacity of infecting directly said cell lines, and, consequently, of enabling the large production of this new retrovirus, for scientific and complementary medicial studies, and, in particular, the perfecting of outfits or "kits" for in vitro diagnosis under acceptable economic conditions.

The invention arises from the discoveries that the LAV retrovirus has no notable cytopathogenic effect with respect to B lymphocytes and that the B lymphocytes can be converted into permanent cell lines which can be infected by a virus called below B-LAV, and produce this virus which has the essential antigen characteristics of the LAV virus, in cultures in suspension, and this in the absence of the TCGF growth factor.

The invention relates more particularly to continuous cell lines of B lymphoblastoid cells characterised by their capacity to be infected by the virus or by an isolate of this retrovirus and to replicate this retrovirus continuously. More particularly, the continuous cell lines of the invention are also directly infectable by a virus or virus isolate having the essential antigen characteristics of the LAV retrovirus, this retrovirus having previously been adapted to B lymphocytes, possibly in the presence of T lymphocytes. More particularly, the invention relates to permanent lymphoblastoid cell lines, whose genetic patrimony comprises at least a portion of that of the Epstein-Barr virus (EBV). However the invention is not limited to this type of B lymphoblastoid cell line. Other lines may be used, for example cell lines derived from Birkitt lymphoma, which can be rendered capable of replicating the abovesaid retrovirus.

The invention also relates to a process for the production of said B lymphoblastoid continuous cell lines suitable for producing continuously the abovesaid retrovirus, this process being characterised by the fact that these continuous lines are infected with a LAV retrovirus previously adapted both to T lymphocytes and B lymphocytes.

Particularly preferred continuous lymphoblastoid cell lines are those which have been obtained by the culture of B lymphocytes, possibly in the presence of T lymphocytes, in the presence of a blastic transformation agent and the LAV retrovirus strain infectious for T lymphocytes. Advantageously, the blastic transformation agent is constituted by the Epstein-Barr virus (EBV). There are thus obtained continuous B lymphoblastoid cell lines rendered capable of replicating a retrovirus having the essential antigen characteristics of the LAV virus. Moreover, these cell lines are revealed to be non-tumorigenic, particularly on the occasion of their innoculation into NUDE mice.

In one embodiment of the process according to the invention for producing continuous B lymphoblastoid cell lines, a co-culture of B lymphocytes and T lymphocytes is formed, from the same donor, in the presence of EBV virus under conditions enabling infection of the B lymphocytes by the EBV virus, preferably in the presence also of an activator facilitating the blastic transformation of the B lymphocytes, and in the presence of LAV virus under conditions normally enabling infection of T lymphocytes.

A preferred activator is constituted by the A protein of *Staphylococcus Aureus*. Naturally any other type activator leading to the same results may be used. The protein A may be replaced by other mitogens, for example lectins, the mitogenic agent such as that known under the expression "Pook-weed mitogen".

Of course the invention is not limited to the use of EBV for inducing the transformation of the lymphocytes into "immortal" B lymphoblastoid lines, in all cases capable of being reproduced through a large number of generations (at least 60 generations) in a suitable culture medium. The EBV may be replaced by other oncogenic transforming DNAs, such as the genes known under the names "Myc" "Erb", etc.

Preferably the infection of the B lymphocytes by the suitable blastic agent, in the presence of T lymphocytes, to transform the first into a lymphoblastoid cell line, precedes the performance of at least one infection operation of the mixture with LAV virus strain.

The B lymphocytes employed in the process according to the invention may be constituted by any type of B lymphoid cells originating from blood or from lymphoid tissues containing B lymphocytes, for example those obtained from bone marrow, from the spleen, from the lymphatic ganglions etc.

In the foregoing it has also been indicated that the B lymphocytes must preferably come from the same donor as the T lymphocytes which have served to propagate the virus. The adaptation of the LAV virus to the B lymphocyte is effected by propagation in several passages, preferably from 8 to 10 passages, of the LAV virus into successive cultures of healthy B and T lymphocytes in admixture, where the B and T lymphocytes are obtained from the same healthy individual.

Additional features of the invention will also appear in the course of the following description of particular embodiments of B lymphoblastoid cell lines producing a retrovirus having the antigen properties of the LAV retrovirus, even if it differs from the latter by a certain number of properties newly acquired and which will be considered below.

The invention relates finally to 3-LAV adapted retroviruses which can be obtained by the the process according to the invention, these retroviruses possessing, besides the antigenic properties characteristic of the LAV retrovirus, the capacity of infecting continuous lines of B lymphoblastoid cells. resulting particularly from the blastic transformation under conditions such as described above, of B lymphocytes previously adapted to T lymphocytes in the presence of a blastic transformation agent, such as EBV virus, or again continuous cell lines of other B lymphomes, such as the Birkitt lymphoma. Viral strains corresponding to these characteristics have been deposited in the National Collection of Microorganism Cultures (CNCM) of the Pasteur Institute of Paris under the same numbers and on the dates which will be indicated below.

Certain preferred viral strains of the invention are characterised also by a density a little higher than that of the LAV virus strain described by F. BARRE SINOUSSI et Coll., particularly of the order of 1.18 in a sucrose gradient.

The advantage of having such strains available is manifest. It enables the direct infection of continuous lines of B lymphoblastoid cells for the production of large amounts of virus. This constitutes the raw material for the production of retrovirus extracts recognisable by serums of patients infected with AIDS or with SLA, particularly for the in vitro diagnosis of these infections, for example under conditions which will be indicated below by way of example. In this respect the invention relates more particularly to extracts of these retroviruses which contain p25 protein, directly recognisable by the serums of the abovesaid patients. The invention extends naturally to outfits or "kits" for the in vitro diagnosis of the abovesaid infections, comprising by way of principal constituent extracts of B-LAV retrovirus.

Additional features of the invention will appear also in the course of the discussion which follows of the techniques which may be employed for arriving both at B lymphoblastoid cell lines which can be rendered capable of continuously producing a virus having the antigenic characteristics of the LAV retrovirus as well as the viral strains concerned.

DETAILED DESCRIPTION

The virus isolated from T lymphocytes of a patient afflicted with lymphadenopathy was first propagated in lymphocytes of the umbilical cord, then in lymphocytes of several adult donors. It had previously been checked that the serums of the donors did not contain antibodies active against the LAV virus and that their lymphocytes were not adapted to release spontaneously LAV virus after activation under the conditions which have been described by BARRE-SINOUSSI et Coll.

The lymphocytes of the particular donor denoted by the initials FR were selected by reason of their capacity to reproduce after infection large and regular amounts of LAV virus. However, as indicated above, the production of LAV virus was in all cases temporary, since it is followed by a reduction, and then by an interruption of the production of the virus and finally the death of the cell cultures.

Production of B lymphoblastoid cell lines capable of producing virus continuously in cultures in suspension have been carried out under the following conditions. It is understood that the culture conditions, then of infection, correspond to those which have been indicated in the article of S. BARRE SINOUSSI et Coll. mentioned above. The complete lymphocytes (B and T lymphocytes in admixture) were first of all stimulated for 24 hours with protein A then infected with a strain of EBV virus, derived from a nasopharyngal carcinoma (strain M 81 described in B.J.A.B. B 95-8 Int J. Cancer 1976 vol. 17 p. 161). Five days later, half of the culture was infected with the LAV virus under the conditions described by BARRE SINOUSSI et Coll. then divided into two sub-cultures $C_1$ and $C_2$. The culture of cells derived from the sub-culture $C_1$ was introduced into a medium devoid of a specific growth factor of T lymphocytes, in particular the factor TCGF. On the other hand, the cells of the $C_2$ sub-culture were cultivated in a medium containing TCGF. The cultures were maintained by the addition of the medium every three days and complete change of medium each week. As foreseen, the cultures stimulated by the TCGF growth factor produced LAV virus detected through the appearance of reverse transcriptase activity in the medium between the 12th day (that is to say on the 6th day after the start of the infection by the LAV virus) and the 21st day. On the other hand, no reverse transcriptase activity was observed in the cell cultures derived from the sub-culture $C_1$ in the absence of the TGCF factor. It was thus clearly established that at this stage the LAV virus could only be produced in detectable amounts by the T lymphocytes activated in the presence of the TCGF growth factor, and this in the absence of detectable virus production by the B lymphocytes.

On the 19th day, at the time of appearance of a decline in the production of the LAV virus, a part $C_2'$ of the culture coming from the sub-culture $C_2$, was placed in contact with T lymphocytes from a fresh T lymphocyte culture which had been obtained from the same donor and which had been activated previously for three days with phytohemaglutinin, and this for the purpose of providing new targets for the virus and to restart the viral infection. Eight days later (25th day), there was in fact observed the appearance of a new type of reverse transcriptase. However, contrary to observations made in the course of the first infection, the production did not stop again. After certain quantitative variations in the production in the course of time, there was observed an increase and a stabilisation of reverse transcriptase activity (greater than 100,000 counts per minute/ml of supernatant). The virus produced was then extracted from cell cultures under the conditions described in the article of BARRE SINOUSSI et Coll. mentioned above.

It will be noted that at the time of restarting the infection by the LAV virus, the appearance of cells transformed by EBV and of larger dimensions have been observed both in the cultures coming from the $C_1$ sub-cultures and in cells coming from $C_2$ sub-cultures. This observation is evidence that the "immortalisation" of the B cells under the action of EBV had already occurred. It remained to determine if the continuous production of LAV retrovirus (or of retrovirus possessing the essential antigenic characteristics thereof) could be attributed to a prolonged survival of the T infected cells in the presence of the lymphoblastoid cell line obtained by transformation of the B lymphocytes by EBV, or on the contrary to the latter. It is to make the necessary discrimination between these two possibilities that the control culture of the cells of the sub-culture $C_1$ was in its turn infected with the virus obtained from the $C_2$ culture (in fact from the frozen supernatant at day 25 of the $C_2$ culture) and maintained in the absence of TCGF. In such a medium the T cell population possibly present could only decline rapidly, which was moreover verified by the absence of a reaction with monoclonal antibodies marketed under the brand OKT4 by the ORTHO company, this absence of reaction testifying, therefore, to the absence of a phenotype characteristic of the T lymphocytes. Consequently the sub-culture producing the virus was essentially constituted by B lymphoblastoid cells.

It may reasonably be inferred from the preceding observations that the new property acquired by the viruses produced by the sub-culture $C_2'$ resulted from the adaptation of the virus to the B lymphocytes contained in the mixture of lymphocytes which had been obtained from the donor FR, before the realisation of the co-infection tests. In fact it has been observed that LAV virus strains obtained after the very first passes in the lymphocytes of FR were not suitable for infecting the B lymphoblastoid line coming from the sub-culture C. On the contrary the LAV viral culture obtained after 10 passes on the lymphocyte mixture of FR is suitable for producing the above-mentioned infection. Other cell lines of B lymphoblastoid cells could be infected under similar conditions. It is true that the infection could not be realised in all the B lymphoblastoid cell lines tested. The Table which follows shows, however, that in 14 lines tested, 5 were productive. A person of ordinary skill in the art would deduce from the Table that continuous production of virus from at least one B lymphoblastoid cell line is either natural or induced from B lymphocytes under the conditions described above. One would also deduce that only a limited number of B lymphoblastoid cell lines would have to be infected. Repeating the tests by infecting different cell lines would be routine for the worker in this field.

This is substantiated by the results in the Table and obtained by in vitro infection tests with B-LAB, of different B lymphoblastoid cell lines produced from lymphocytes obtained from adults or from umbilical cords previously infected with strains of EBV NPC (M 81) or (B 95/8). LAV virus production has been obtained from B lymphoblastoid cells obtained from an umbilical cord lymphocyte culture (LCo), from lymphocytes of another BAR donor (that is to say from lymphocyte cultures coming from two donors out of four). It is to be noted that the B-LAV virus derived from the B lymphoblastoid cell line of the donor FR appeared more rapidly and at a higher titer. This result suggests that the B-LAV viral strain had indeed undergone secondary adaptation to B cells after its passage in the initial FR lymphocyte mixture.

Other cell lines obtained from (natural) B lymphoblastoid cells, particularly cancerous lines having certain of the phenotypes of B lymphocytes, have also been tested for their liability to infection by LAV and B-LAV viruses. Only the BJAB strain (not previously infected by EBV) has been infected by B-LAV after a prolonged period of 30 days. On the other hand, the same strain could not be infected under the same conditions by the initial LAV strain. However, the prior in vitro transformation of the same cell line with the strain B 95/8 of EBV has permitted potentiation of the subsequent production by the same line of B-LAV virus. In fact, there has been observed a reproduction yield of B-LAV virus 2 to 3 times higher than in the case of the BJAB line described in Biomedicine 1975, vol. 2, 22, p. 276, not previously transformed by EBV.

Certainly the table shows the other "natural" cell lines could not be affected. However, it is quite remarkable that the cell lines which produced the B-LAV virus formed it in the absence of any growth factor, whether it was specific to T lymphocytes or B lymphocytes.

type B lines, it is preferable to add periodically about 50% of new uninfected cells when the viral production starts to decline (about every 2 months).

Analysis of the morphological and immunological characteristics of B-LAV strains has led to the conclusion that they all possess the characteristics of the LAV strains initially employed and described in the article by S. BARRE SINOUSSI et Coll. In addition, they show the characteristic of being able to infect the abovesaid B lymphoblastoid cell lines. Certain of the strains, in particular those obtained from the donor FR8, exhibit a density a little higher than the initial strain (1.18 instead of 1.17 in a glucose gradient).

More detailed examination of the cell lines producing B lymphoblastoid cells confirms the relationship to the B lines. These cells have the markers characteristic of B lymphocytes (specific immunoglobulins present at the surface). The cells obtained from B lymphocytes infected with EBV all possessed the EBNA antigen (abbreviation of the expression "Epstein-Barr nuclear antigen"). An expression of the precocious antigen (EA) has been observable in 0.1% of the cells of the LCo line and in 3.5% of the FR8 lines. None of the cells of the NCo line produced a positive response in the detection tests of the viral capsid antigen. This antigen was, however, present in 1.5% of the cells of the FR8 line.

As regards finally the various B-LAV virus preparations, it has been observed that their respective nucleic acids did not lead to any hybridization with DNA probes containing the G fragment coding for the early

TABLE

| Cell Lines | Origin | Presence of EBV Genome | LAV Retrovirus | B-LAV Growth | CNCM |
|---|---|---|---|---|---|
| FR 8 | B lymphocytes from adult donor | yes | ++ | ++ | I-303 |
| BAR | B lymphocytes from adult donor | yes | + | ++ | |
| BRA | B lymphocytes from adult donor | yes | — | — | |
| DIER | B lymphocytes | yes | — | — | |
| LCo | umbilical cord B lymphocyte | yes | + | ++ | I-302 |
| LC1 | umbilical cord B lymphocyte | yes | — | — | |
| Daudi | Burkitt lymphomas | yes | — | — | |
| Namalwa | Burkitt lymphomas | yes | — | — | |
| Raji | Burkitt lymphomas | yes | — | — | |
| Chev | Burkitt lymphomas | yes | — | — | |
| BJAB | Burkitt lymphomas | no | — | + | I-300 |
| BJAB/B95/8 | Burkitt lymphomas | yes | — | ++ | I-301 |
| MOLT/4 | T lymphomas | no | — | — | |
| HL60 | myeloid leukemia | no | — | — | |

The foregoing cell lines were the subject of deposits at the National Collection of Microorganisms of Institut Pasteur, Paris, France, which is abbreviated CNCM on May 9, 1984 under the above indicated numbers. The B-LAV virus itself was deposited at the CNCM on the same data under number I-299.

When the capacity of cell cultures to produce B-LAV virus has been determined, B-LAV virus strains can be isolated from supernatants of the cell cultures, and the B-LAV virus strains can then be again propagated in other cell lines of lymphoblastoid cells. Although LAV does not show cytopathogenic effects on antigen EA (abbreviation of the expression "early antigen") in the tests carried out on a cellulose filter. It follows that the retrovirus preparations obtained do not exhibit a detectable contamination by the genome of the EBV virus.

The invention relates lastly to a method of in vitro diagnosis of SLA or of AIDS, this method comprising the contacting of a serum or other biological medium coming from a patient presumed to have been able to have been infected and the detection of the immunological reaction possibly produced.

The preferred ways of employing this method utilize immunoenzymatic or immunofluorescent tests, particularly by the ELISA technique. Consequently, the invention also relates to viral extracts provided with a marker, for example, an enzymatic marker, fluorescent marker, radioactive marker, etc.

The diagnostic tests can comprise the following operations:

deposition of predetermined amounts of an extract according to the invention in cups of a microplate for titration;

introduction into these cups of increasing dilutions of serum submitted to the diagnosis;

incubation of the microplate;

thorough washing of the microplate;

introduction into the cups of the microplate of antibodies marked and directed against blood immunoglobulins, the marking being preferably carried out by an enzyme capable of hydrolysing a substrate, hydrolysis employing modification of the absorption of said substrate of certain bands of predetermined wavelengths and detection, preferably by comparison with controls, of the amount of substrate hydrolysed, the measurement obtained resulting in an evaluation of the risk to which the patient is exposed or of the actual presence of the disease.

In consequence the invention relates also to outfits or "kits" to perform the abovesaid diagnosis in vitro, these outfits comprising:

an extract or a further purified fraction of the B-LAV virus, this extract and this fraction being marked, for example by a radioactive, enzymatic, or immunofluorescent label;

human anti-immunoglobulins or protein A (advantageously fixed to a support insoluble in water, for example agarose beads);

a lymphocyte obtained from a healthy donor; and buffers and, if necessary, substrates to permit the marker to made visible.

There will also be described below and purely by way of example, preferred constitutions of the reagents which can be used for the in vitro diagnosis and the conditions of their employment.

Principle of the method

An ELIZA test is brought into action for the detection and the titration of type LAV anti-retrovirus serum antibodies.

It is carried out by a competition test between the viral antigen (cultivated on B lymphoblastoid cells) and the control antigen constituted by a lysate of the same uninfected cells.

The fixation of the antibodies to the two antigens is revealed by the use of a human antiglobulin marked by an enzyme, itself revealed by an addition of a corresponding substrate.

Preparation of viral antigen

The cellular cultures used are B lymphoblastoid cells of human origin, infected with B-LAV under the above-indicated conditions.

The supernatant liquor from cells infected by the virus is used. It is concentrated by precipitation to PEG 10%, successively purified on saccharose gradients (20° to 60°) by ultra-centrifugation to equilibrium.

The viral fractions are collected and concentrated by centrifugation=50,000 RPM for 60 minutes.

The pellet of the virus is taken up again in a minimum volume of NTE buffer pH=7.4 (Tris 0.015M-NaCl 0.1M-EDTA 1 milliMolar).

The protein concentration is determined by the Lowry method.

The virus is then lysed by a RIPA+SDS (0.5% final) buffer for 15 minutes at 37° C. The RIPA buffer is described in Science 1983, vol. 220, page 868–871. It is possible to use for the lysis of the virus the following modification: 1% solution of TRITON×100 and 0.1% of sodium desoxycholate in RIPA buffer, prepared without SDS.

The virus is then lysed by a RIPA+SDS (0.5% final) buffer for 15 minutes at 37° C.

Preparation of the control antigen

The B lymphoblastoid cells in culture, but uninfected, according to the preceding conditions for 5 to 10 days, are centifuged at low speed and lysed in the RIPA buffer in the presence of 5% of the compound marketed under the trademark ZYMOFREN (Special) namely 500 U/ml. After a treatment of 15 minutes a 4° C. with frequent shaking in the vigorous shaking device known under the name VORTEX, the lysate is centrifuged at 10,000 RPM. The supernatant liquor constitutes the control antigen. Its concentration of protein is measured by the Lowry method.

Reagents

1—Plates=NUNC—special controlled ELISA

2—PBS Buffer: pH=7.5

3—Wetting agent marketed under the trademark TWEEN 20

4—Carbonate buffer:

$$\text{pH} = 9.6 \begin{bmatrix} CO_3Na_2 = 0.2\ M \\ CO_3HNa = 0.2\ M \end{bmatrix}$$

5—Non fetal calf serum: preserved frozen (Biopro)

6—Bovine serum albumin (BSA) SIGMA (fraction V)

7—anti-IgG (H+L) marked with peroxidase of Pasteur Institute=1 ml bottles—conservation +4° C.

8—Washing buffer=PBS buffer pH 7.5±0.05% TWEEN 20 Dilution of the conjugate=dilution indicated in PBS+TWEEN 20 (0.05%)+Bovine albumin 0.5 g per 100 ml.

9—Dilution buffer of the serums=PBS buffer+0.05% TWEEN 20

10—Substrate=EPO $$\text{Citrate buffer pH} = 5.6 \begin{bmatrix} \text{citrate trisodium } (C_6H_5Na_4O_3.2H_2O) \\ \text{(Merck) 0.05 M} \\ \text{acid citric } (C_6H_8O_7.1H_2O) \\ \text{(Merck) 0.05 M} \end{bmatrix}$$

Hydrogen peroxide=at 30% (110 volumes)—used at 0.03% at the time of use in citrate buffer.

Ortho-phenylene-diamine: SIGMA.

75 mg per 25 ml buffer—To be diluted in citrate buffer extemporaneously.

Preparation of ELISA plates 96 cup U-bottom plates (NUNC=ELISA) were used. They comprised 12 columns, numbered 1 to 12 respectively, of 8 cups.

The distribution of the antigens was done under the following conditions:

100 µl of the viral antigen diluted with carbonate buffer pH=9.6 were deposited in each cup of columns:

1-2-5-6-9-10

The cups of these columns are denoted below by the expression "cups +".

In the same way 100 µl of the control antigen diluted in the carbonate buffer pH=9.6 were deposited in cups of the columns:

3-4-7-8-11-12

The cups of the latter columns are denoted below by the expression "cups −".

The dilution of the viral antigen is checked at each viral production. Several viral antigen dilutions were tested as a function of known positive and negative controls (at several dilutions) and is a function of the human anti-IgG marked with peroxidase, tested also at several dilutions.

As a general rule, the protein concentration of the preparation was 5 to 2.5 µ/ml.

The same protein concentration was used for the control antigen.

The plates were closed by means of plastic covers and were incubated overnight at +4° C.

They were then placed once in distilled water and then well drained. The cups were then filled with 300 µl 20% fetal calf serum in PBS buffer.

The incubation lasted two hours at 37° C. (covered plates).

The plates were washed three times in PBS+TWEEN 20, 0.05%=PBS-tw.

First washing 300 µl
2nd and 3rd washings 200 µl/cup

The plates can be drained, then sealed with adhesive plastic film and preserved at −80° C. ELISA Reaction=Search in titration of antibodies:

After thawing, the plates were washed three times in PBS-tw. They were drained and dried.

The positive and negative control serums, as well as the tested serums, were diluted in tubes previously, in PBS-tw 0.05% Bovin albumin at 0.5%.

The dilution selected was 1/40.

100 µl of each serum was deposited in duplicate on the viral antigen and in duplicate on the control antigen.

The same for the diluted positive and negative serums.

100 µl of PBS+TWEEN+Bovine albumin were deposited the same way in 2 "cups +" and 2 "cups −" to constitute the conjugate control.

The plates provided with their covers were incubated one hour 30 minutes at 37° C. They were washed 4 times in PBS=TWEEN 0.05%

100 µl of human anti-IgG (marked with peroxidase) at the selected dilution, were deposited in each cup and incubated at 37° C.

The plates were again washed 5 times with PBS+TWEEN. They were drained and dried.

The development of the enzymatic reaction was carried out by means of an ortho-phenylenediamine substrate (0.05% of citrate buffer pH 5.6 containing 0.03% $H_2O_2$).

100 µl of substrate were distributed in each cup.

The plates were placed in the dark for 20 minutes at laboratory temperature.

Readings were made with a spectrophotometer (for microplates at 492 nm).

Serums that were deemed to possess antibodies against this virus were those having a difference in optical density (between the optical density of the viral antigen and the optical density of the control antigen) higher than or equal to 0.30%.

This technique permits qualitative as well as quantitative determinations to be made. For this, it is possible either to carry out dilutions of the serums to be tested, or to compare a dilution of the serum with a range of tested controls under the same conditions.

We claim:

1. A continuous cell line from a culture of human B lymphoblastoid cells, wherein the cells have the following characteristics:
   (a) Lymphadenopathy Associated Virus (LAV) is not cytotoxic to the cells;
   (b) When the cells are cultured, supernatant from the cells exhibits reverse transcriptase activity;
   (c) The cells do not immunologically react with monoclonal antibodies to Leu-3 cells;
   (d) When the cells are cultured in the absence of T cell growth factor (TCGF), infected cells continuously produce B-LAV retrovirus, which is a retrovirus having the essential antigenic characteristics of LAV.

2. Cell line as claimed in claim 1, wherein the cells do not contain the genome of Epstein-Barr virus (EBV).

3. Cell line as claimed in claim 1, wherein the cells contain at least part of the genome of Epstein-Barr virus (EBV).

4. Cell line as claimed in claim 1, wherein the cells are derived from a Burkitt lymphoma.

5. Cell line as claimed in claim 1, wherein the cells contain Epstein-Barr nuclear antigen (EBNA).

6. A process for producing a continuous cell line of B lymphoblastoid cells, wherein the process comprises:
   (a) providing a cell culture medium comprising human B lymphocytes;
   (b) contacting the B lymphocytes in the culture medium with an oncogenic transforming agent under conditions to form a continuous cell line of transformed B lymphoblastoid cells; and
   (c) contacting the transformed B lymphoblastoid cells with Lymphadenopathy Associated Virus (LAV) under conditions in which the transformed B lymphoblastoid cells are infected with LAV;
   wherein the B lymphoblastoid cells after infection with LAV produce B-LAV, which is a retrovirus having the essential antigenic characteristics of LAV.

7. A process as claimed in claim 6, wherein the transformed B lymphoblastoid cells are subject to multiple infections with LAV.

8. A process for producing a continuous cell line of B lymphoblastoid cells, wherein the process comprises:
   (a) providing a cell culture medium comprising a mixture of human T lymphocytes and human B lymphocytes;
   (b) contacting the T lymphocytes and B lymphocytes in the culture medium with Epstein-Barr virus as a transforming agent under conditions to form a continuous cell line of transformed B lymphoblastoid cells; and (c) contacting the transformed B lymphoblastoid cells with Lymphadenopathy Associated Virus (LAV) under conditions in which the transformed B lymphoblastoid cells are infected with LAV;

wherein the B lymphoblastoid cells after infection with LAV produce B-LAV, which is a retrovirus having the essential antigenic characteristics of LAV.

9. A process as claimed in claim 8, wherein the transformed B lymphoblastoid cells are subject to multiple infections with LAV.

10. A process for producing a continuous cell line of B lymphoblastoid cells, wherein the process comprises:
(a) providing a cell culture medium comprising a mixture of human T lymphocytes and human B lymphocytes;
(b) contacting the T lymphocytes and B lymphocytes with a mitogen under conditions to facilitate blastic transformation of the B lymphocytes;
(c) contacting the lymphocytes from step (b) with Epstein-Barr virus (EBV) as a transforming agent under conditions to form a continuous cell line of transformed B lymphoblastoid cells;
(d) contacting the transformed B-lymphoblastoid cells with Lymphadenopathy Associated Virus (LAV) under conditions in which the transformed cells are infected with LAV; and
(e) cultivating the resulting LAV-infected cells to obtain a sustained level of reverse transcriptase activity in the culture;

wherein the B lymphoblastoid cells after infection with LAV produce B-LAV, which is a retrovirus having the essential antigenic characteristics of LAV.

11. A process as claimed in claim 10, wherein the transformed B lymphoblastoid cells are subject to multiple infections with LAV.

12. Process as claimed in claim 11, wherein the T lymphocytes and the B lymphocytes are from the same human donor.

13. Process as claimed in claim 11, wherein the nitrogen is Protein A of *Staphylococcus Aureus*.

14. Process as claimed in claim 11, which comprises the additional steps of:
cultivating the LAV-infected B lymphoblastoid cells with T cell growth factor (TCGF) to obtain a culture medium that exhibits reverse transcriptase activity;
after reverse transcriptase activity declines, contacting the culture medium with fresh T lymphocytes to proliferate viral infection; and
cultivating the resulting cells under conditions to obtain a sustained level of reverse transcriptase activity in the culture medium.

15. Process as claimed in claim 14, wherein all of the lymphocytes are from the same human donor.

16. Process as claimed in claim 15, wherein the fresh lymphocytes are activated with phytohemaglutinin prior to contact with the culture medium.

17. Process as claimed in claim 15, wherein the B lymphocytes are derived from umbilical cord lymphocytes.

18. Process as claimed in claim 11, wherein the B lymphocytes are derived from a Burkitt lymphoma.

19. A retrovirus termed B-LAV, which is comprised of antigen and the antigen is immunologically recognized by sera of a patient afflicted with Lymphadenopathy Syndrome (LAS) or Acquired Immune Deficiency Syndrome (AIDS), and wherein the retrovirus:
(a) exhibits reverse transcriptase activity with a strong affinity for poly(adenylate-oligodeoxythymidylate)[poly(A)-oligo(dT)$_{12\text{-}18}$] with $Mg^{2+}$;
(b) exhibits tropism for T-lymphocytes;
(c) exhibits preferential tropism for Leu-3 cells;
(d) is cytopathic to Leu-3 cells infected with the retrovirus;
(e) induces the production of p25 viral protein of Lymphadenopathy Associated Virus (LAV) in T-lymphocytes infected with LAV;
(f) exhibits slight antigenic homology with the virus of infectious anemia of the horse (VAIC), in that antibody against VAIC immunoprecipitates p25 viral protein of LAV; and
(g) is capable of infecting continuous B lymphoblastoid cell lines having C.N.C.M. Deposit Accession Nos. I-300, I-301, I-302, and I-303, and of being replicated by said cell lines when cultured;

wherein the retrovirus is in biologically pure form.

20. Retrovirus as claimed in claim 19, wherein the retrovirus has an average diameter of 139 nanometers and an eccentric nucleus having an average diameter of 41 nanometers.

21. A method of amplifying a retrovirus, wherein the retrovirus is B-LAV, said method comprising:
(a) contacting a continuous cell line of human B lymphoblastoid cells as claimed in claim 19 with B-LAV; and
(b) culturing the cells in suspension in the absence of T cell growth factor (TCGF) and under conditions in which the retrovirus proliferates.

22. Method as claimed in claim 21, wherein the method includes the further step of separating B-LAV from the cultured cells in step (b).

23. Method as claimed in claim 21, wherein the cell line has the identifying characteristics of C.N.C.M. Deposit Accession No. I-300.

24. Method as claimed in claim 21, wherein the cell line has the identifying characteristics of C.N.C.M. Deposit Accession No. I-301.

25. Method as claimed in claim 21, wherein the cell line has the identifying characteristics of C.N.C.M. Deposit Accession No. I-302.

26. Method as claimed in claim 21, wherein the cell line has the identifying characteristics of C.N.C.M. Deposit Accession No. I-303.

27. A retrovirus having the identifying characteristics of C.N.C.M. Deposit Accession No. I-299.

28. A continuous cell line of human B lymphoblastoid cells having the identifying characteristics of C.N.C.M. Deposit Accession No. I-300.

29. A continuous cell line of human B lymphoblastoid cells having the identifying characteristics of C.N.C.M. Deposit Accession No. I-301.

30. A continuous cell line of human B lymphoblastoid cells having the identifying characteristics of C.N.C.M. Deposit Accession No. I-302.

31. A continuous cell line of human B lymphoblastoid cells having the identifying characteristics of C.N.C.M. Deposit Accession No. I-303.

* * * * *